United States Patent
Iriyama et al.

(10) Patent No.: US 9,579,310 B2
(45) Date of Patent: Feb. 28, 2017

(54) ARTIFICIAL SKIN

(71) Applicant: Shiseido Company, Ltd., Chuo-ku, Tokyo (JP)

(72) Inventors: Shunsuke Iriyama, Yokohama (JP); Kenichi Umishio, Yokohama (JP); Makoto Tsunenaga, Yokohama (JP); Shinji Inomata, Yokohama (JP); Eijiro Adachi, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 3 days.

(21) Appl. No.: 14/496,534

(22) Filed: Sep. 25, 2014

(65) Prior Publication Data

US 2015/0011593 A1 Jan. 8, 2015

Related U.S. Application Data

(62) Division of application No. 13/582,199, filed as application No. PCT/JP2011/050887 on Jan. 19, 2011, now Pat. No. 8,871,505.

(30) Foreign Application Priority Data

Mar. 4, 2010 (JP) .................. 2010-048159

(51) Int. Cl.
| | | |
|---|---|---|
| *A61F 2/10* | (2006.01) | |
| *C12N 5/071* | (2010.01) | |
| *A61L 27/60* | (2006.01) | |
| *A61K 31/4406* | (2006.01) | |
| *A61L 27/38* | (2006.01) | |
| *A61K 31/4184* | (2006.01) | |
| *A61L 27/36* | (2006.01) | |

(52) U.S. Cl.
CPC .......... *A61K 31/4406* (2013.01); *A61F 2/105* (2013.01); *A61K 31/4184* (2013.01); *A61L 27/362* (2013.01); *A61L 27/3804* (2013.01); *A61L 27/3813* (2013.01); *A61L 27/3886* (2013.01); *A61L 27/60* (2013.01)

(58) Field of Classification Search
None
See application file for complete search history.

(56) References Cited

U.S. PATENT DOCUMENTS

2009/0317441 A1* 12/2009 Bilbo .............. A61B 17/12122
                                                     424/423
2011/0020477 A1   1/2011 Iriyama

FOREIGN PATENT DOCUMENTS

| CN | 101588808 A | 11/2009 |
|---|---|---|
| EP | 1 281 396 A2 | 2/2003 |
| JP | 2001-269398 A | 10/2001 |
| WO | WO 99/03979 A1 | 1/1999 |
| WO | WO 2008/046162 A1 | 4/2008 |
| WO | WO 2009/123215 A1 | 10/2009 |

OTHER PUBLICATIONS

Contard et al. "Culturing keratinocytes and fibroblasts in a three-dimensional mesh results in epidermal differentiation and formation of a basal lamina-anchoring zone", Journal of Investigative Dermatology 100 (1): 35-39, 1993.*
Amano et al., "MMP Inhibitors Markedly Enhance Basement Membrane Formulation in Skin-Equivalent Model," The Journal of Investigative Dermatology, Apr. 1, 2000, 114(4):822, No. 435.
Canty et al., "Actin Filaments Are Required for Fibripositor-mediated Collagen Fibril Alignment in Tendon," J. Biol. Chem., Dec. 15, 2006, 281(50):38592-38598.
Fleischmajer et al., "Immunochemistry of a Keratinocyte-Fibroblast Co-culture Model for Reconstruction of Human Skin," J. Histochemistry and Cytochemistry, 1993, 41(9):1359-1366.
Humphries et al,. "Active Negative Control of Collagen Fibrillogenesis in Vivo," J. Biol. Chem., May 2, 2008, 283(18):12129-12135.
Iriyama et al., (WO 2009/123215) EPO translation.
Ishihara, M., "Mammalian Heparanase: Breaking Down Barrier in Tumor Invasion and Metastasis," Trends in Clycoscience and Glycotechnology, Sep. 1999, 11(61):297-298.
Pan et al., "1-[4-(1H-Benzoimidazol-2-yl)-phenyl]-3-[4-(1H-benzoimidazol-2-yl)-phenyl]-urea derivatives as small molecule heparanase inhibitors," Bioorganic & Medicinal Chemistry Letters, 2006, 16:409-412.
Amano et al., "Protective effect of matrix metalloproteinase inhibitors against epidermal basement membrane damage: skin equivalents partially mimic photoageing process," British Journal of Dermatology, 2005, 153(Suppl. 2):37-46.

* cited by examiner

*Primary Examiner* — Emily Cordas

(74) *Attorney, Agent, or Firm* — Foley & Lardner LLP

(57) ABSTRACT

The present invention relates to a method for producing artificial skin, comprising: adding a matrix metalloproteinase inhibitor and a heparanase inhibitor to an artificial skin formation culture medium comprising human epidermal keratinocytes and human dermal fibroblasts, culturing the cells in the artificial skin formation culture medium, and forming artificial skin.

3 Claims, 3 Drawing Sheets

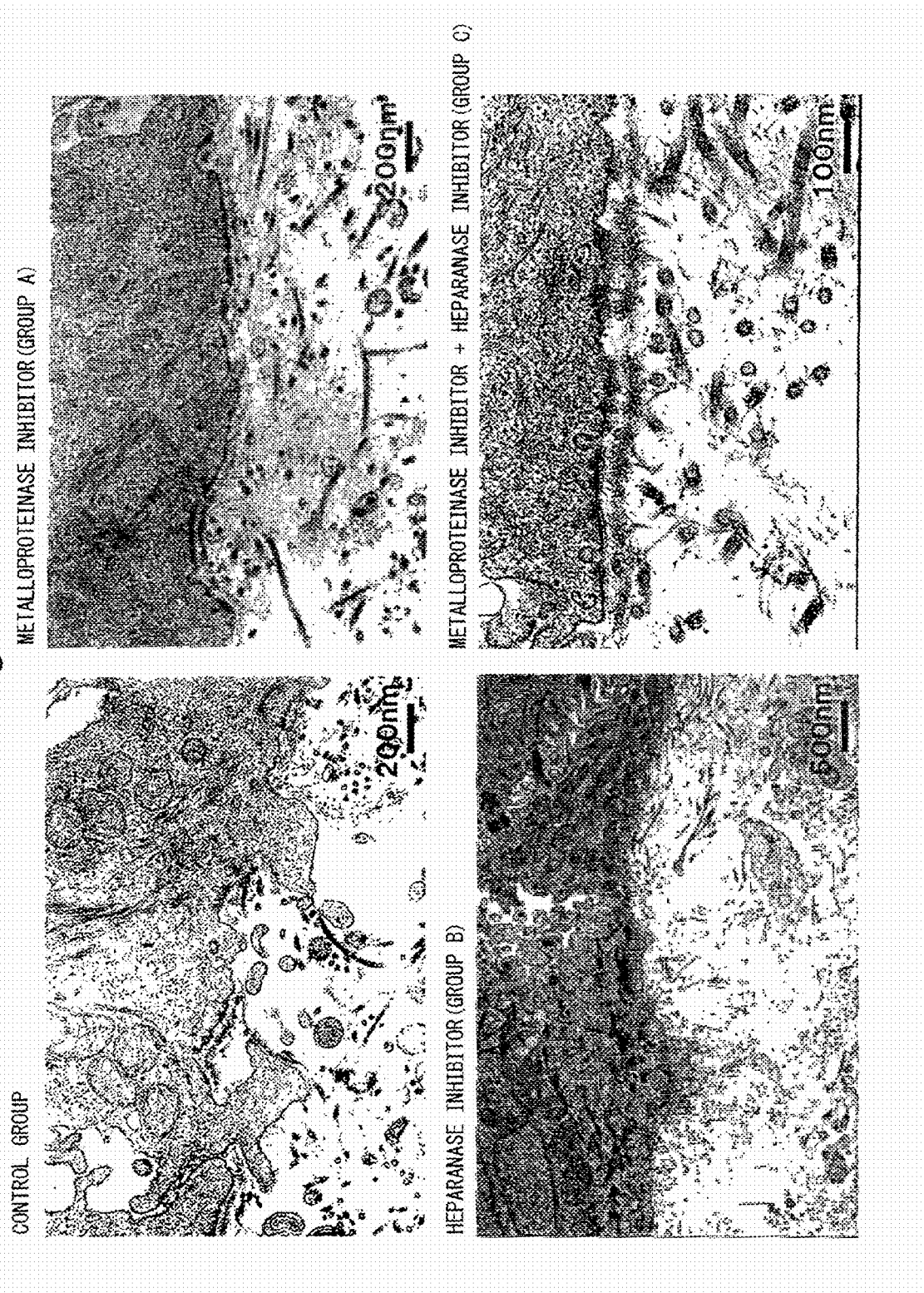

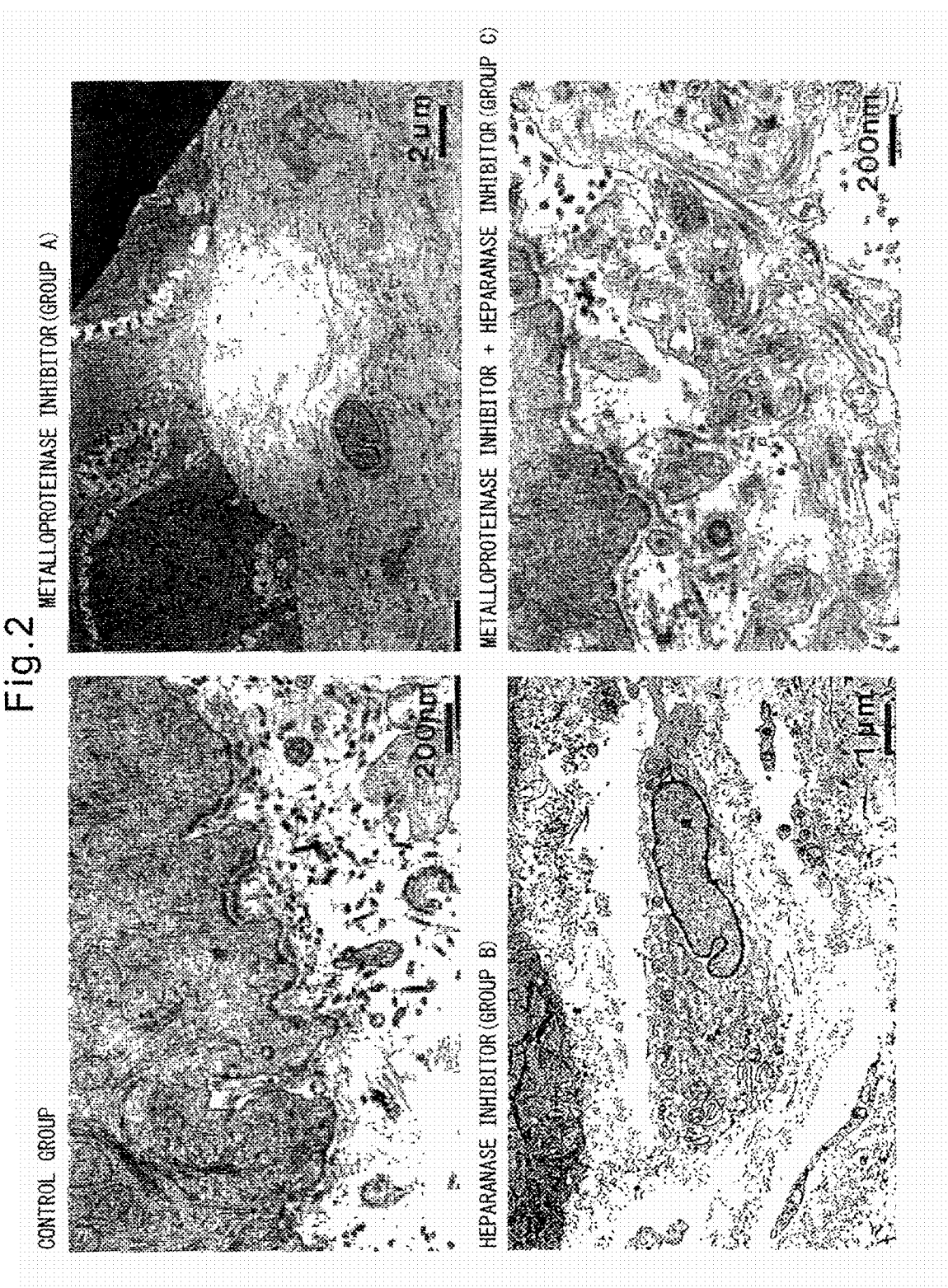

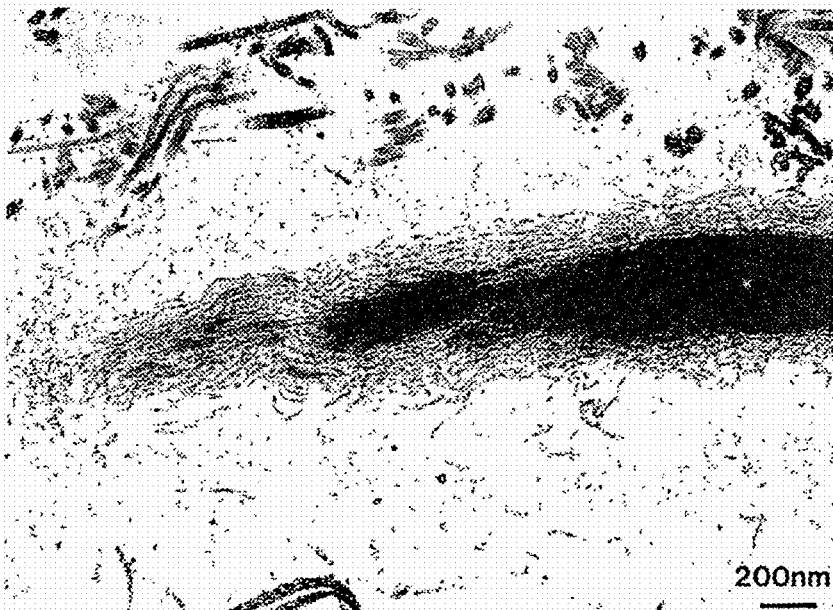

ARTIFICIAL SKIN

CROSS-REFERENCE TO RELATED APPLICATIONS

This application is a Divisional of U.S. application Ser. No. 13/582,199, which is the U.S. National Stage application of PCT/JP2011/050887, filed Jan. 19, 2011, which claims priority from Japanese application JP 2010-048159, filed Mar. 4, 2010.

TECHNICAL FIELD

The present invention relates to a novel method for producing artificial skin comprising the use of a matrix metalloproteinase inhibitor and a heparanase inhibitor, and to novel artificial skin produced according to that method.

BACKGROUND ART

Skin covers the entire bodies of various animals, including humans, and is exposed to the formation of wrinkles, hardening, age spots, darkening and decreased elasticity and the like caused by aging and external factors such as sunlight, dryness, oxidation, environmental stress and psychological stress.

Natural skin is broadly composed of two layers consisting of the epidermis and the dermis, and a thin, minute membrane referred to as the epidermal basement membrane is present between the epidermis and dermis. The epidermal basement membrane is an extremely thin structure having a thickness of about 0.1 μm, and is present in the form of a sheet at the junction between the epidermis and dermis. In addition to the epidermal basement membrane having a basic structure comprised of the lamina densa and lamina lucida, it is also composed of keratinocyte hemidesmosomes, anchoring fragments, anchoring fibers and the like, and in particular, the basic structure thereof is composed of, for example, type IV collagen and various types of laminins and proteoglycans. The main component of epidermal basal cells and the basic structure, and particularly the anchoring fragments bound to the lamina densa, is laminin-5, and the basic structure and dermal collagen fibers are connected by anchoring fibers composed mainly of type VII collagen. In addition, the anchoring fragments and anchoring fibers are mutually bound, and form complexes referred to as anchoring complexes. As a result of having such a structure, the skin, which is present on the outermost layer of the body, maintains a degree of strength capable of withstanding external mechanical stress (Encyclopedia of Cosmetics, Society of Cosmetic Chemists of Japan, pp. 405-406).

However, there is a growing demand for artificial skin to be used as a substitute in the case original skin (namely, natural skin) has become damaged for some reason. In addition, it is also extremely important to develop artificial skin for use as an experimental material for testing the action of pharmaceuticals and cosmetics on the skin, and in either of these applications, there is a strong desire for artificial skin that mimics the structure of natural skin as closely as possible.

A known method for producing artificial skin of the prior art consists of culturing normal human epidermal keratinocytes on a shrunken collagen gel containing human fibroblasts to form an epidermal layer. However, in this method, since a basement membrane is not adequately formed between the collagen gel that mimics the dermis and the epidermal layer that mimics the epidermis, in the case of using this artificial skin, reformation of skin basement membrane was promoted by the administration of a matrix metalloproteinase or both a matrix metalloproteinase and a matrix protein production promoter (Japanese Unexamined Patent Publication No. 2001-269398). In addition, substances that inhibit serine proteases, type IV or type VII collagen, which is the main constituent of the epidermal basement membrane, or substances that enhance the production output of laminin-5 are known to promote the basement membrane formation promoting effects of matrix metalloproteinase inhibitors (Japanese Unexamined Patent Publication No. 2004-75661). However, in the case of this artificial skin produced according to the prior art, the formation of higher-order structures of the epidermal basement membrane and the dermis remains undeveloped, thereby preventing adequate communication between the epidermal basement membrane and the dermis.

In addition, although compounds that inhibit heparanase are known to improve basement membrane function in the body and thereby inhibit the formation of wrinkles in the process by which wrinkles are formed in the skin (International Publication No. WO 2009/123215), the combination of these compounds with a matrix metalloproteinase inhibitor is not known to promote the reformation of epidermal basement membrane and dermis in artificial skin.

PRIOR ART DOCUMENTS

Patent Documents

Patent Document 1: Japanese Unexamined Patent Publication No. 2001-269398
Patent Document 2: Japanese Unexamined Patent Publication No. 2004-75661
Patent Document 3: International Publication No. WO 2009/123215

SUMMARY OF THE INVENTION

Problems to be Solved by the Invention

An object of the present invention is to provide artificial skin in which communication between the epidermal basement membrane and dermis is adequately achieved and is as close as possible to the structure of natural skin.

Means for Solving the Problems

When the inventor of the present invention formed artificial skin by adding a matrix metalloproteinase inhibitor and a heparanase inhibitor to an artificial skin formation culture medium comprising human epidermal keratinocytes and human dermal fibroblasts and culturing the cells in the culture medium, the inventor of the present invention succeeded in obtaining artificial skin in which higher-order structures of the epidermal basement membrane and dermis approximated those of natural skin extremely closely.

Thus, the present application includes the inventions indicated below.

[1] A method for producing artificial skin, comprising: adding a matrix metalloproteinase inhibitor and a heparanase inhibitor to an artificial skin formation culture medium comprising human epidermal keratinocytes and human dermal fibroblasts, culturing the cells in the artificial skin formation culture medium, and forming artificial skin.

[2] Artificial skin, comprising: an epidermal basement membrane containing a continuous lamina densa and anchoring fibers arising from the lamina densa, and a dermis containing collagen fibers; wherein, the epidermal basement membrane and the dermis are securely adhered by bonding of the anchoring fibers arising from the continuous lamina densa present in the epidermal basement membrane to the collagen fibers present in the dermis.

[3] The artificial skin described in [2] above, wherein the dermis further contains fibripositors.

[4] The artificial skin described in [2] or [3] above, wherein elastic fibers are formed in the dermis.

[5] The artificial skin described in any of [2] to [4] above, which is produced according to the method described in [1] above.

[6] Artificial skin consisting of artificial cells formed in a culture medium containing a matrix metalloproteinase inhibitor and a heparanase inhibitor; wherein, the artificial cells comprise an epidermal basement membrane containing a continuous lamina densa and anchoring fibers arising from the lamina densa, and a dermis containing collagen fibers, and the epidermal basement membrane and the dermis are securely adhered by bonding of the anchoring fibers arising from the continuous lamina densa present in the epidermal basement membrane to the collagen fibers present in the dermis.

Effects of the Invention

The formation of a continuous, uniform lamina densa not observed in artificial skin of the prior art and anchoring fibers bound to the lamina densa was surprisingly confirmed within the epidermal basement membrane of artificial skin obtained according to the method of the present invention. Moreover, fibripositors, which had previously only been reported in natural skin, were observed in the dermis of the artificial skin, and the formation of elastic fibers, which are extremely difficult to reconstruct using conventional methods, was also confirmed. These higher-order structures of the epidermal basement membrane and dermis approximate those of natural skin extremely closely.

BRIEF DESCRIPTION OF THE DRAWINGS

FIG. 1 depicts electron micrographs showing the structures of basement membranes of a control group, a skin model cultured by adding only a matrix metalloproteinase (MMP) inhibitor to a culture fluid (group A), a skin model cultured by adding only a heparanase inhibitor to a culture fluid (group B) and a skin model cultured by adding both an MMP inhibitor and heparanase inhibitor to a culture fluid (group C).

FIG. 2 depicts electron micrographs showing fibroblasts present in dermis directly beneath a basement membrane of a control group, a skin model cultured by adding only a matrix metalloproteinase (MMP) inhibitor to a culture fluid (group A), a skin model cultured by adding only a heparanase inhibitor to a culture fluid (group B) and a skin model cultured by adding both an MMP inhibitor and heparanase inhibitor to a culture fluid (group C). In contrast to the fibroblasts being normal fibroblasts in the control group, group A and group B, the fibroblasts contain fibripositors in group C.

FIG. 3 is an electron micrograph showing elastic fibers formed in the dermis of a skin model cultured by adding both an MMP inhibitor and heparanase inhibitor to a culture fluid (group C).

EMBODIMENTS OF THE INVENTION

Matrix Metalloproteinase (MMP) Inhibitor

There are no particular limitations on the matrix metalloproteinase inhibitor used in the present invention provided it is a substance having inhibitory activity against matrix metalloproteinases. Examples of matrix metalloproteinases include gelatinase, collagenase, stromelysin and matrilysin. Thus, a substance that inhibits gelatinase, collagenase, stromelysin or matrilysin and the like can be selected for use as the matrix metalloproteinase inhibitor.

Specific examples of matrix metalloproteinase inhibitors include substance CGS27023A (N-hydroxy-2-[[(4-methoxyphenyl)sulfonyl](3-picolyl)amino]-3-methylbutanamide hydrochloride) (J. Med. Chem., 1997, Vol. 40, pp. 2525-2532), and MMP-inhibitor (p-NH2-Bz-Gly-Pro-D-Leu-Ala-NHOH) (FN-437) (BBRC, 1994, Vol. 199, pp. 1442-1446). Substance CGS27023A is preferably used for the matrix metalloproteinase inhibitor.

Heparanase Inhibitor

There are no particular limitations on the heparanase inhibitor used in the present invention provided it is a substance that has inhibitory activity against heparanase. Heparanase is an enzyme that is present in various cells that specifically decomposes heparan sulfate chains of various heparan sulfate proteoglycans. In the skin, heparanase is produced by epidermal keratinocytes that compose the epidermis, fibroblasts of the dermis, and intravascular endothelial cells.

A specific example of a heparanase inhibitor is 1-[4-(1H-benzoimidazol-2-yl)-phenyl]-3-[4-(1H-benzoimidazol-2-yl)-phenyl]-urea.

Artificial Skin

Any arbitrary culture medium conventionally used in the production of artificial skin can be used for the basal medium used to produce artificial skin in the present invention, and examples of these culture media include Dulbecco's Modified Eagle's Medium (DMEM) containing 10% fetal bovine serum, DMEM-Ham's F-12 (3:1) medium containing 10% fetal bovine serum, 5 μg/ml of transferrin, 5 μg/ml of insulin, 2 nM triiodothyronine, 0.1 nM cholera toxin and 0.4 μg/ml of hydrocortisone, and culture medium consisting of a 1:1 mixture of keratinocyte growth medium (KGM) and DMEM containing 10% fetal bovine serum. Although varying according to the type thereof, the amount of matrix metalloproteinase inhibitor added to these basal media is typically about 10 μg/L to 10 g/L, preferably about 100 μg/L to 1 g/L, and optimally about 1 mg/L to 100 mg/L. In addition, although also varying according to the type thereof, the amount of heparanase inhibitor added to these basal media is typically about 10 μg/L to 100 g/L, preferably about 100 μg/L to 10 g/L, and optimally about 1 mg/L to 1 g/L.

In the production of artificial skin of the present invention, a shrunken type I collagen gel containing human fibroblasts is first allowed to stand undisturbed on a metal mesh. The shrunken type I collagen gel containing human fibroblasts can be prepared, for example, in the manner described below. After producing a collagen solution containing suspended fibroblasts on ice, the collagen is gelled in a Petri dish to prepare a gel. Subsequently, the gel is peeled from the walls of the Petri dish and the collagen gel is allowed to shrink in a $CO_2$ incubator.

Next, epidermal cells such as normal human epidermal keratinocytes are cultured on the collagen gel to form an epidermis. Formation of an epidermal layer by culturing skin cells can be carried out in the manner described below. A shrunken collagen gel is placed on a metal mesh followed by placing a glass ring over the gel. A suspension of human preputial epidermal keratinocytes was placed in the glass ring to prevent leakage of liquid. The ring was removed after the keratinocytes adhered in the $CO_2$ incubator. The aforementioned culture medium was filled to the boundary of the epidermal layer, and culturing was continued while exposing the epidermal layer to air to form a horny layer.

According to this method, artificial skin that approximates the structure of natural skin extremely closely can be obtained within the extremely short time period of about 1 day to 4 weeks, and typically about 4 days to 2 weeks, after the start of culturing. More specifically, the formation of a continuous, uniform lamina densa as well as anchoring fibers bound to the lamina densa, which had not been observed in artificial skin of the prior art, were confirmed in the epidermal basement membrane of the artificial skin of the present invention.

The lamina densa serves as the basic structure of the epidermal basement membrane and is composed of type IV collagen, various types of laminins and proteoglycans. Anchoring fibers mainly composed of type VII collagen arise from the basic structure thereof in the form of the lamina densa, and these have the function of securely connecting the epidermal basement membrane and dermis by intertwining with collagen fibers of the dermis. Thus, the formation of a continuous lamina densa in the epidermal basement membrane of the artificial skin of the present invention and the formation of anchoring fibers arising from the lamina densa means that the artificial skin of the present invention has an extremely high degree of strength with respect to external mechanical stress in the same manner as natural skin.

More surprisingly, the formation of higher-order structures of fibroblasts characterized by developed rough-surfaced endoplasmic reticulum and fibripositors was confirmed in the dermis of the artificial skin of the present invention. Secretory proteins are known to be synthesized by membrane-bound ribosomes present within rough-surfaced endoplasmic reticulum. In addition, fibripositors are known to contain collagen fibrils and function as actin-rich protoplasmic membrane projections protruding from fibroblasts, and collagen fibrils have been reported to be deposited in extracellular channels formed by adjacent fibroblasts by these fibripositors (Elizabeth G. Canty, et al., The Journal of Cell Biology, Vol. 165, No. 4, 2004, pp. 553-563, Elizabeth G. Canty, et al., The Journal of Biological Chemistry, Vol. 281, No. 50, Dec. 15, 2006, Sally M. Humphries, et al., The Journal of Biological Chemistry, Vol. 283, No. 18, pp. 12129-12135, and Zoher Kapacee, et al., Matrix Biology, Vol. 27, 2008, pp. 371-375). Thus, the fact that fibroblasts having developed rough-surfaced endoplasmic reticulum and fibripositors therewithin are present in the dermis of the artificial skin of the present invention indicates that the function of fibroblasts present in the reformed dermis of the artificial skin is significantly activated by matrix metalloproteinase inhibitor and heparanase inhibitor, and means that the production of the cell matrix in the form of secretory protein synthesis and collagen fibers is actively occurring in the artificial skin of the present invention in the same manner as in natural skin.

More importantly, the formation of elastic fibers, for which reconstruction has been extremely difficult in conventional artificial skin, was confirmed in the dermis of the artificial skin of the present invention. Elastic fibers are mainly composed of microfibrils and amorphous elastin, and in natural skin, mature elastic fibers are distributed between mesh-like layers of collagen fibers. The primary function of elastic fibers is to impart elasticity to the skin and maintain skin tightness. In addition, microfibrils running perpendicular directly beneath the basement membrane fulfill the important role of connecting the basement membrane to the dermis. Thus, the formation of elastic fibers in the dermis of the artificial skin of the present invention is extremely important evidence indicating that the artificial skin of the present invention has a function similar to that of natural skin.

The artificial skin of the present invention can be clinically transplanted as a substitute for natural skin in the case the body's natural skin is subjected to lesions or damage for some reason. In addition, the artificial skin of the present invention can be applied aesthetically to irregular skin surfaces in order to correct kelloid scars caused by burns, skin graft scars, surgical scars, deep wrinkles, deep wound scars, acne scars, large hair follicles or fine lines in the skin and the like. Moreover, the artificial skin of the present invention can also be used for skin hypersensitivity testing and testing of efficacy or toxicity of pharmaceuticals and cosmetics, or for research on wound healing, cell migration, cancer cell invasion, cancer cell metastasis or cancer progression and the like.

As has been described above, since the combination of a matrix metalloproteinase inhibitor and heparanase inhibitor realizes higher-order structures of the epidermal basement membrane and dermis of artificial skin that approximate those of natural skin extremely closely, the combination thereof is useful as a culture fluid for forming the artificial skin of the present invention. Thus, in another aspect of the present invention, an artificial skin culture fluid is provided that comprises a matrix metalloproteinase inhibitor and a heparanase inhibitor. In addition, in the case of applying a matrix metalloproteinase inhibitor and heparanase inhibitor to skin of the body, regeneration and repair of the epidermal basement membrane and dermis are thought to be promoted. Thus, in still another aspect of the present invention, a skin activation composition for promoting the regeneration and repair of the epidermal basement membrane and/or dermis that comprises one or a plurality of matrix metalloproteinase inhibitors and heparanase inhibitors. Here, "skin activation" refers to the prevention and improvement of, for example, decreased skin function accompanying structural changes in the epidermal basement membrane and/or dermis attributable to aging and the like, and more specifically, the prevention and improvement of skin wrinkling and hardening.

The aforementioned artificial skin culture fluid or skin activation composition contains as active ingredients thereof contain a matrix metalloproteinase inhibitor and heparanase inhibitor at concentrations that are sufficient for promoting regeneration and repair of the epidermal basement membrane and dermis, and these active ingredients are typically respectively contained at 0.0000001% by weight to 10% by weight, and preferably 0.000001% by weight to 10% by weight, based on the weight of the culture fluid or composition.

In addition, a vehicle such as that used when preparing the aforementioned artificial skin culture fluid or skin activation composition, as well as fragrances, oils, surfactants, antiseptics, metal ion sequestering agents, water-soluble polymers, thickeners, powdered ingredients, ultraviolet absorbers, moisturizers, pharmaceutical ingredients, antioxidants, pH adjusters, cleansing agents, drying agents or emulsions and the like can also be suitably incorporated in the artificial skin culture fluid or skin activation composition. In the case of incorporating each of these ingredients in the artificial skin culture fluid or skin activation composition of the present invention, it is necessary to incorporate these ingredients within a range that does not impair the desired effects of the present invention.

EXAMPLES

1. Skin Model Culturing Method

A skin model (EFT-400, MatTeK) was cultured in a specialized medium (EFT-400-ASY, MatTeK). Dimethylsulfoxide (DMSO) and ethanol were added to the specialized medium to a final concentration of 0.1% to serve as a control group, 50 mM 1-[4-(1H-benzoimidazol-2-yl)-phenyl]-3-[4-(1H-benzoimidazol-2-yl)-phenyl]-urea (DMSO solvent) was added to the specialized medium to a final concentration of 50 µM to serve as a heparanase inhibitor group, 10 mM N-hydroxy-2-[[(4-methoxyphenyl)sulfonyl](3-picolyl)amino]-3-methylbutanamide hydrochloride (CGS27023A, ethanol solvent) was added to the specialized medium to a final concentration of 10 µM to serve as an MMP inhibitor group, and 50 mM 1-[4-(1H-benzoimidazol-2-yl)-phenyl]-3-[4-(1H-benzoimidazol-2-yl)-phenyl]-urea (DMSO solvent) and 10 mM CGS27023A (ethanol solvent) were added to the specialized medium to a final concentration of 50 µM and 10 µM, respectively, to serve as a heparanase inhibitor+MMP inhibitor group, followed by culturing.

2. Electron Microscope Observations

The aforementioned skin model was cut in half after culturing, fixed with Zamboni's fixative and post-fixed with osmic acid, followed by embedding in resin in accordance with established methods. Tissues were observed by preparing ultra-thin sections and staining with uranyl acetate followed by observing with an electron microscope (JEM-1230, JEOL). The morphologies of the skin model cultured by adding solvents to ordinary culture fluid (control group), the skin model cultured by adding only MMP inhibitor in the form of N-hydroxy-2-[[(4-methoxyphenyl)sulfonyl](3-picolyl)amino]-3-methylbutanamide hydrochloride (CGS27023A) to the culture fluid (group A), the skin model cultured by adding only heparanase inhibitor in the form of 1-[4-(1H-benzoimidazol-2-yl)-phenyl]-3-[4-(1H-benzoimidazol-2-yl)-phenyl]-urea to the culture fluid (group B), and the skin model cultured by adding both N-hydroxy-2-[[(4-methoxyphenyl)sulfonyl](3-picolyl)amino]-3-methylbutanamide hydrochloride (CGS27023A) and 1-[4-(1H-benzoimidazol-2-yl)-phenyl]-3-[4-(1H-benzoimidazol-2-yl)-phenyl]-urea to the culture fluid (group C) were then compared. The results are shown in the following table.

TABLE 1

| Structural Characteristics of Dermis Models | Continuity of Lamina Densa Structure | Formation of Anchoring Fiber Structures | Formation of Elastic fibers | Appearance of Fibripositors |
|---|---|---|---|---|
| Control Group | X | — | — | — |
| Group A | Δ | — | — | — |
| Group B | Δ | — | — | — |
| Group C | ⊙ | ⊙ | ⊙ | ⊙ |

⊙: Definite continuity, Δ: weak continuity, X: No continuity, —: not observed

Among the structures observed in normal human skin, the formation of anchoring fiber structures was observed only in group C, namely the skin model in which both MMP inhibitor and heparanase inhibitor were added to the culture fluid. In addition, the appearance of fibripositors, which were unable to be realized in previously reported skin models and which play an important role in formation of skin matrix, was also only observed in group C. Moreover, the appearance of elastin, the structures of which are formed directly beneath the basement membrane of the skin models, was also only observed in group C. These results indicate that the skin model group C approximates natural skin to a greater extent than ever before.

The invention claimed is:

1. Artificial skin, comprising: an epidermal basement membrane containing a continuous lamina densa and anchoring fibers arising from the lamina densa, and a dermis containing collagen fibers; wherein the anchoring fibers arising from the lamina densa are securely bonded to the collagen fibers in the dermis, and wherein the dermis further comprise fibripositors.

2. The artificial skin according to claim 1, wherein elastic fibers are present in the dermis.

3. Artificial skin, comprising: an epidermal basement membrane containing a continuous lamina densa and anchoring fibers arising from the lamina densa, and a dermis containing collagen fibers, wherein the epidermal basement membrane and the dermis are securely adhered by bonding of the anchoring fibers arising from the continuous lamina densa present in the epidermal basement membrane to the collagen fibers present in the dermis, which is produced according to a method for producing artificial skin, comprising: adding a matrix metalloproteinase inhibitor and a heparanase inhibitor to an artificial skin formation culture medium comprising human epidermal keratinocytes and human dermal fibroblasts, culturing the cells in the artificial skin formation culture medium, and forming artificial skin.

* * * * *